United States Patent [19]

Schaper et al.

[11] Patent Number: 4,652,401

[45] Date of Patent: Mar. 24, 1987

[54] SALICYLIC ACID ESTERS AS PERFUMES

[75] Inventors: Ulf-Armin Schaper; Benno Streschnak, both of Krefeld; Siegfried Bloesl, Duesseldorf; Walter Sommer, Krefeld, all of Fed. Rep. of Germany

[73] Assignee: Henkel Kommanditgesellschaft auf Aktien, Duesseldorf, Fed. Rep. of Germany

[21] Appl. No.: 689,629

[22] Filed: Jan. 8, 1985

[30] Foreign Application Priority Data

Feb. 8, 1984 [DE] Fed. Rep. of Germany ....... 3404310

[51] Int. Cl.[4] ................ A61K 7/46

[52] U.S. Cl. ................ 252/522 R; 568/67

[58] Field of Search ................ 252/522 R, 522 A; 568/67

[56] References Cited

U.S. PATENT DOCUMENTS 3,714,227 1/1973 Ueno et al. ................ 560/67

4,276,431 6/1981 Schnegg et al. ................ 560/67

FOREIGN PATENT DOCUMENTS 406225 9/1922 Fed. Rep. of Germany .

OTHER PUBLICATIONS

S. Arctander, "Perfume and Flavor Chemicals", 1969, Nos. 218,529,530,1680,1906.

G. Fenaroli, "Fenaroli's Handbook of Flavor Ingredients", 1971, p. 407.

Chemical Abstract 91, 1979, "Monographs on Fragrance Raw Materials".

Chemical Abstract 92, 1980, "Monographs on Fragrance Raw Materials cis-3-Hexenyl Salicylate".

S. Arctander, Perfume and Flavor Chemicals, 1969; P. Z. Bedoukian, Perfum. Flavor 6 (5), 60–61, (1981), vol. I.

S. Arctander, Perfume and Flavor Chemicals, 1969; P. Z. Bedoukian, vol. II.

*Primary Examiner*—Werren B. Lone

*Attorney, Agent, or Firm*—Ernest G. Szoke; Henry E. Millson, Jr.; Mark A. Greenfield

[57] ABSTRACT

Perfume and fragrance compositions containing salicylic acid esters, of which the ester function is derived from secondary or primary branched-chain, saturated aliphatic alcohols containing 6 C-atoms.

8 Claims, No Drawings

SALICYLIC ACID ESTERS AS PERFUMES

BACKGROUND OF THE INVENTION

1. Field of the Invention

This invention relates to salicylic acid esters having perfume properties, to their use as perfumes, and to perfume compositions containing them.

2. Description of Related Art

Numerous esters of salicylic acid are known from the literature. Some of them, including for example the methyl, butyl, amyl, hexyl, benzyl and 3-hexenyl esters of salicylic acid, are used in the perfume industry (S. Arctander, Perfume and Flavor Chemicals, 1969; P. Z. Bedoukian, Perfum. Flavor 6 (5) 60–61 (1981)).

DESCRIPTION OF THE INVENTION

A new group of salicylic esters distinguished by surprising and valuable perfume properties, particularly by very high persistence, has now been found. This new group of salicylic acid esters are the salicylic acid esters of secondary or primary, branched-chain, saturated aliphatic alcohols. The esters are characterized by the following general formula

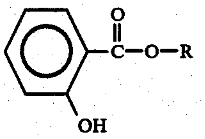

(I)

in which R is the residue of a secondary or a primary branched-chain, saturated aliphatic alcohol containing 6 C-atoms. Examples of such esters are 2-hexyl salicylate, 2-ethylbutyl salicylate, and 2-methylpentyl salicylate.

The esters are of particular interest by virtue of their pronounced odor profile.

The salicylic acid esters are produced in known manner by esterifying salicylic acid with a secondary or primary branched-chain, saturated aliphatic alcohol corresponding to the above formula in the presence of acidic catalysts, the water given off during the reaction being removed; or by reacting salicylic acid chloride with the alkali alcoholate of the particular alcohol; or by transesterifying methyl salicylate with the particular alcohol in the presence of alkaline catalysts.

The compounds corresponding to the general formula are known from the literature although there is no reference there to their properties as perfumes.

The odor characteristics of the salicylic acid esters of formula I is general flowery-sweet and balsamy with a typical salicylate note, with flowery, honey-like, herbal notes crucially determining the odor profile in individual cases.

The esters of formula I are distinguished by extremely high stability of their odor profile. They do not produce any unpleasant secondary odors, even after prolonged storage of the products perfumed with them. By virtue of their pleasing odor and their persistence coupled with their high stability, the claimed esters are particularly suitable for use under practical conditions.

The claimed esters can be combined with other perfumes and/or standard perfume excipient ingredients to form new interesting perfume compositions. To this end, the compounds are used in a quantity of from about 1 to about 50% by weight, based on the composition as a whole. Compositions such as these may be used for perfuming cosmetics, such as toilet waters, creams, lotions, aerosols, toilet soaps, in extract perfumery and also for improving the odor of industrial products, such as cleaners, disinfectants, fabric treatment preparations and the like. By virtue of their unusual power of performance and tenacity, the esters are particularly suitable for perfuming fabric detergents, fabric softeners and cosmetics. The above ester compositions are added to the various products in quantities of from about 0.05 to about 2% by weight, based on the product as a whole.

The invention will be illustrated but not limited by the following examples.

EXAMPLES

General procedure for the esterification process 1 mole of salicylic acid methyl ester, 2 moles of the particular $C_6$ alcohol and 18 g (0.1 mole) of a 30% sodium methylate solution were initially introduced into a reaction vessel. The methanol released was distilled off through a destillation head at 120° C. The sump temperature rose to approximately 170° C.

On completion of the transesterification reaction, the residue was taken up in water and extracted with ether. The ether extract was washed until neutral, dried over sodium sulfate, and concentrated.

The crude product gave the desired ester after distillation through a packed column.

| | | | |
|---|---|---|---|
| 1. | 2-hexyl salicylate | $B.p._{1.08}$ | 108° C. |
| | | $n_D^{20}$ = | 1.5038 |
| | Odor: sweet faintly balsamy, honey note | | |
| 2. | 2-ethylbutyl salicylate | $B.p._{0.03}$ | 103° C. |
| | | $n_D^{20}$ = | 1.5080 |
| | Odor: clean, fresh-flowery, herbal-green note | | |
| 3. | 2-methylpentyl salicylate | $B.p._{0.01}$ | 90° C. |
| | | $n_D^{20}$ = | 1.5059 |
| | Odor: green-flowery note. | | |

4. BALSAMY ORIENTAL PERFUME BASE

| | |
|---|---|
| 25 | Coumarin |
| 25 | Heliotropin |
| 50 | Moschus ketone |
| 40 | Ethyl vanillin |
| 3 | Evernyl (a trademark of RBD) |
| 17 | Labdanum Resin |
| 20 | Styrax Honduras |
| 2 | Aldehyde C 14 so-c., pure |
| 50 | Amyl cinnamic aldehyde (alpha) |
| 30 | Eugenol pure |
| 50 | Hydroxy citronellal pure |
| 10 | Isoraldein 70 (a trademark of Givaudan) |
| 5 | Sandalore (a trademark of Givaudan) |
| 30 | Benzyl acetate |
| 20 | Citronellol pure |
| 50 | Linalyl acetate |
| 100 | Tert.-butyl cyclohexyl acetate |
| 50 | Bergamot synthetic |
| 25 | Elemi oil |
| 100 | Orange oil sweet |
| 50 | Patchouli oil Singapore |
| 25 | Boisambrene forte (a trademark of Henkel KGaA) |
| 50 | Irotyl (a trademark of Henkel KGaA) |
| 25 | Hedione (a trademark of Firmenich) |
| 30 | Mandarin oil |
| 25 | Geranium oil Bourbon |
| 10 | Ambroxan (a trademark of Henkel KGaA) 10% |
| 83 | 2-ethylbutyl salicylate |
| 1,000 | |

5. Perfuming of soap 2-ethylbutyl salicylate was incorporated in soap chips in a concentration of 1.5%. The forearm of a test subject was washed with the soap of 15 seconds and the odor of the lather assessed. The lather was then rinsed off, the forearm dried and the remaining odor assessed over a period of several hours.

The known perfume, benzyl salicylate, was used for comparison. Power of emanation and persistence were assessed on a scale of 1 to 6 in which:

6=very strong performance and tenacity
5=strong performance and tenacity
4=good performance and tenacity
3=still noticeable performance and tenacity
2=very weak performance and tenacity
1=no performance or tenacity

TABLE 1

| | Odor of lather | Odor of skin |
|---|---|---|
| 2-ethylbutyl salicylate | 5 | 5 |
| Benzyl salicylate (Comparison perfume) | 3 | 3 |

6. Perfuming a fabric softener 0.3% of 2-ethylbutyl salicylate was incorporated as perfume in the formulation of a standard, commercially available fabric softener based on cation-active quaternary ammonium compounds, emulsifiers, viscosity regulators, solvents and diluents.

A formulation perfumed with 0.3% of benzyl salicylate was used for comparison.

Three different cloths of cotton (CN), polyester (PE) and cotton/polyester blend (M) were rinsed with 100 ml of this fabric softener in a washing machine. After spin-drying, the cloths were assessed for odor both in moist form and after drying (overnight on a washing line) (cf Example 5). In addition, the cloths were stored under dry conditions (in polyethylene bags) and reassessed after various periods.

TABLE 2

| | Fabric | Moist | Dried over-night | +24 h | +1 week | +2 week |
|---|---|---|---|---|---|---|
| 2-ethylbutyl-salicylate | CN | 6 | 5 | 4 | 3 | 2 |
| | PE | 6 | 4 | 4 | 3 | 2 |
| | M | 5 | 4 | 3 | 3 | 1 |
| Benzyl salicylate | CN | 4 | 3 | 2 | 3 | 1 |
| | PE | 4 | 3 | 2 | 2 | 1 |
| | M | 3 | 3 | 2 | 2 | 1 |

The rating numbers have the same meaning as in Example 5 above.

7. Perfuming a detergent 0.15% of 2-ethylbutyl salicylate was incorporated as a perfume in the formulation of a standard commercially available heavy-duty detergent based on anionic and nonionic surfactants, builders, complexing agents, perborate, redeposition inhibitors, soil suspending agents, brighteners and fillers. A second sample of the same detergent was perfumed with 0.15% of benzyl salicylate for comparison.

Normally soiled washing was washed with the detergents in a drum-type washing machine using the pre-wash and main-wash cycles.

On completion of the pre-wash and main-wash cycles, (a) the wash liquor was assessed for odor after rinsing and spin-drying, (b) the damp washing was assessed for odor in the same way as described in Example 5.

TABLE 3

| | Odor of the wash liquor pre-wash | Odor of the wash liquor main-wash | Damp washing |
|---|---|---|---|
| 2-ethylbutyl salicylate | 5 | 6 | 3 |
| Benzyl salicylate (comparison perfume) | 2 | 2 | 2 |

What is claimed is:

1. In a perfume or fragrance composition, the improvement comprising adding thereto an odor enhancing quantity of at least one salicylic acid ester of the formula

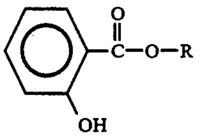

wherein R is a residue of a secondary or primary branched-chain, saturated aliphatic alcohol containing 6 C-atoms.

2. A composition in accordance with claim 1 wherein the salicylic acid ester is one or more of 2-hexyl salicylate, 2-ethylbutyl salicylate or 2-methylpentyl salicylate.

3. A composition in accordance with claim 1 wherein the composition from about 1 to about 50% by weight of the at least one salicylic acid ester.

4. A process for imparting a pleasant odor to a substance comprising adding thereto a sufficient quantity of at least one salicylic acid ester of the formula

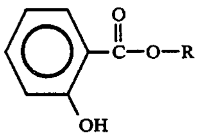

wherein R is a residue of a secondary or primary branched-chain, saturated aliphatic alcohol containing 6 C-atoms to impart said pleasant odor thereto.

5. A process in accordance with claim 4 wherein the salicylic acid ester is one or more of 2-hexyl salicylate, 2-ethylbutyl salicylate or 2-methylpentyl salicylate.

6. A process for imparting a pleasant odor to a substance comprising adding thereto an odor imparting quantity of the composition of claim 1.

7. A process for imparting a pleasant odor to a substance comprising adding thereto an odor imparting quantity of the composition of claim 2.

8. A process for imparting a pleasant odor to a substance comprising adding thereto an odor imparting quantity of the composition of claim 3.

* * * * *